United States Patent
Scott et al.

(10) Patent No.: US 6,403,524 B2
(45) Date of Patent: *Jun. 11, 2002

(54) FLUORINATION CATALYST AND PROCESS

(75) Inventors: John David Scott, Cuddington; Michael John Watson, Eaglescliffe; Graham Ramsbottom, Eccleston, all of (GB)

(73) Assignee: Imperial Chemical Industries PLC, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,500

(22) PCT Filed: Sep. 4, 1997

(86) PCT No.: PCT/GB97/02372

§ 371 (c)(1), (2), (4) Date: Mar. 8, 1999

(87) PCT Pub. No.: WO98/10862

PCT Pub. Date: Mar. 19, 1998

(30) Foreign Application Priority Data

Sep. 10, 1996 (GB) ............................................. 9618857
Sep. 10, 1996 (GB) ............................................. 9618858
Sep. 10, 1996 (GB) ............................................. 9618865

(51) Int. Cl.[7] .......................... B01J 23/26; C07C 17/07; C07C 17/013

(52) U.S. Cl. ...................... 502/307; 502/305; 502/306; 502/319; 570/164; 570/165; 570/169; 570/170

(58) Field of Search ................................. 502/305, 306, 502/307, 319; 570/319, 164, 165, 169, 170

(56) References Cited

U.S. PATENT DOCUMENTS

| | | | | |
|---|---|---|---|---|
| 4,912,270 A | * | 3/1990 | Carlson et al. | 570/169 |
| 5,414,167 A | * | 5/1995 | Bragante et al. | 570/177 |
| 5,475,168 A | * | 12/1995 | Masiero et al. | 570/177 |
| 5,494,873 A | * | 2/1996 | Tsuji et al. | 502/319 |
| 5,849,658 A | * | 12/1998 | Shibanuma et al. | 502/228 |

FOREIGN PATENT DOCUMENTS

| | | | |
|---|---|---|---|
| AU | 80340/94 | | 6/1995 |
| EP | 0502605 | * | 9/1992 |
| EP | 0641598 | * | 3/1995 |
| EP | 0657408 | * | 6/1995 |

* cited by examiner

*Primary Examiner*—Elizabeth D. Wood
(74) *Attorney, Agent, or Firm*—Cook, Alex, McFarron, Manzo, Cummings & Mehler, Ltd.

(57) ABSTRACT

A chromia-based fluorination catalyst in which the chromia is at least partially crystalline and which may contain a zinc or a compound thereof, the production of the catalyst by sintering amorphous chromia and its use in fluorination processes.

21 Claims, No Drawings

FLUORINATION CATALYST AND PROCESS

This invention relates to a fluorination catalyst and the production and use thereof and particularly to an improved fluorination catalyst based on chromia, a process for producing the catalyst and a fluorination process using the catalyst.

Fluorination processes comprising reaction of a starting material with hydrogen fluoride to introduce one or more fluorine atoms into the starting material are well known and are used extensively in industry. Vapour phase processes in which the starting material and hydrogen fluoride are reacted in the vapour phase at elevated temperature are common and such processes usually employ a fluorination catalyst which often is a catalyst comprising or based on chromia which has been subjected to a pretreatment with hydrogen fluoride to provide the working catalyst. It is generally accepted that chromium oxide catalysts of high surface area and wherein the chromium is present as chromium (III) have high initial activity and that such active chromia catalysts are in an amorphous or essentially amorphous state. A recent development in chromia catalysts is a catalyst of enhanced activity produced by incorporating an activity-promoting amount of a divalent metal oxide such as an oxide of zinc, nickel or cobalt, especially zinc, in the catalyst, the oxide or at least the chromia remaining in the essentially amorphous state and having a large surface area. Catalysts containing other divalent metal oxides such as magnesia have also been proposed.

When used in the production of hydrofluorocarbons [HFCs], the known chromia catalysts and especially those promoted by a divalent metal such as zinc have a high initial activity and can result in high conversions and high selectivities. They suffer from a progressive reduction in activity due to deposition of coke on the catalyst but they can be regenerated a number of times by heating in an oxygen-containing atmosphere such as air or a mixture of air with hydrogen fluoride and have a reasonable and generally acceptable lifetime. However, the catalysts suffer the disadvantage that they are not particularly robust, especially in respect of chemical robustness and are deteriorated under the conditions of use and especially when subjected to high temperatures in the presence of hydrogen fluoride so that their lifetime leaves something to be desired.

The present invention is based on the discovery that the robustness of chromia—based catalysts and hence their useful working lifetimes is increased by inducing or introducing crystallinity and preferably a controlled degree of crystallinity into the chromia. Moreover, the initial activity of the catalysts can be slightly but significantly enhanced, without a reduction in selectivity, by introducing an activity-promoting amount of zinc or a compound of zinc into the catalyst.

According to the first aspect of the invention there is provided an improved chromia-based fluorination catalyst wherein the chromia is at least partially crystalline.

Preferably, the chromia exhibits an apparent degree of crystallinity as represented by alpha chromia type crystals greater than 8%, preferably greater than 20%, and less than 50% by weight.

Introducing crystallinity into the chromia results in a decrease in the surface area of the catalyst and too high a degree of crystallinity results in an unacceptably low surface area, for example below 20 $m^2/gm$. The degree of crystallinity in the catalyst can be controlled so as to result in a catalyst having a surface area greater than about 20 $m^2/gm$, preferably from about 30 to about 70 $m^2/gm$.

According to a further aspect of the invention, there is provided an improved zinc-promoted chromia fluorination catalyst wherein the chromia is at least partially crystalline and the catalyst comprises zinc or a compound of zinc in an amount of less than about 3% by weight of the catalyst.

In a further aspect of the invention there is provided an improved zinc-promoted chromia-based fluorination catalyst wherein the chromia is at least partially crystalline produced by inducing crystallinity in chromia and subsequently introducing zinc or a compound of zinc into the crystallised chromia by impregnation with a solution of a soluble zinc salt. The catalyst preferably contains from 0.1% to about 2% by weight of zinc or a compound of zinc depending upon the degree of crystallinity induced in the chromia.

Inducing crystallinity in the chromia results in a decrease in the surface area of the catalyst and a very high a degree of crystallinity results in a very low surface area, for example below 10 $m^2/gm$. The degree of crystallinity in the catalyst of the invention can be controlled such that the catalyst has a surface area greater than about 20 $m^2/gm$, preferably from about 30 to about 70 $m^2/gm$.

Suitably, the catalyst according to the first aspect of the invention contains zinc or a compound of zinc. A catalyst according to the invention may contain an activity-promoting amount of a divalent metal such as cobalt, magnesium or nickel or a compound thereof in addition to or instead of zinc or a zinc compound. Nevertheless, the preferred metal is zinc and in this case the amount of the zinc is important since it is known that zinc can act as a catalyst poison if present in too large an amount. We have found that whilst the activity-promoting amount of zinc in catalysts wherein the chromia is amorphous is generally greater than about 2% by weight and usually greater than about 5% by weight depending upon the method of production of the catalyst, the activity promoting amount of zinc in the partially crystallised catalysts of the invention should generally be less than about 2% by weight, preferably no greater than about 1% by weight.

According to a preferred embodiment of the invention there is provided a chromium-based fluorination catalyst comprising from 0.1 to 2% by weight of zinc or a compound of zinc wherein the chromia is at least partially crystalline. The catalyst preferably has an apparent degree of crystallinity as represented by alpha chromia type crystals of from about 8% to about 50% and has a surface area greater than about 20 $m^2/gm$.

If present, the amount of divalent metal other than zinc in the catalyst, whether the divalent metal be an activity promotor or not, is not critical since such metals are not generally regarded as catalyst poisons even if present in large amounts. The amount of such metals may vary over a wide range up to 50% by weight or even higher of the catalyst, although the amount will usually be in the range from about 5% to about 25% by weight.

The apparent degree of crystallinity or the degree of crystallinity induced in the chromia is determined by X-ray diffraction analysis using the standard NIST [National Institute of Standards and Technology] technique and comparing the result with that obtained by analysis of a pure alpha chromia standard prepared by sintering chromia at 1223 k in air for 24 hours (100% crystallinity). The catalysts do not have a true alpha chromia structure so that the % degree of crystallinity determined by comparison with the results for pure alpha chromia is not a true % degree of crystallinity and therefor is referred to herein as the "apparent degree of crystallinity". Morover, since the catalyst structure is not true alpha chromia so that the X-ray diffraction peak tends to be slightly distorted, the apparent degree of crystallinity is expressed herein as being represented by "alpha chromia type crystals".

The apparent degree of crystallinity as represented by alpha chromia type crystals is determined by measuring the integrated area of the 104 peak of both the catalyst sample and the pure alpha chromia standard (at ca. 33.6 °2θ for Cu K radiation) between 32.5 and 35.0°2θ, subtracting the background to provide corrected integrated areas and then ratioing the corrected area for the catalyst sample to the corrected area for the standard sample.

The catalyst exhibits an X-ray diffraction peak at a spacing of lattice planes from 2.65 to 2.7 of half maximum peak width less than 0.8 degrees.

Preferably the chromium in the catalyst is present as chromium (III) although a small amount, say up to 10%, of chromium (VI) may be present as a result of the conditions under which the chromia is crystallised. As described hereinafter, crystallinity can be induced in the chromia by sintering the catalyst at elevated temperature and this may be carried out under an inert atmosphere or in the presence of air. Catalysts produced by sintering in an inert atmosphere tend to comprise essentially chromium (III) but require higher sintering temperatures whilst those produced by sintering in air tend to contain some chromium (VI) but require lower sintering temperatures. We prefer to sinter the catalysts under an atmosphere of air or a mixture of air and nitrogen since these conditions enable relatively low temperatures of 300° C. to 450° C. to be employed.

The catalyst of the invention has excellent activity and selectivity and has improved chemical robustness leading to a long working lifetime. However, the catalyst lacks the physical robustness or toughness associated with amorphous chromia catalysts and is difficult to handle in practice, for example it is not readily produced in the form of pellets in which fluorination catalysts are usually produced and it does not easily withstand temperature shocks as are often encountered in the operation of large-scale industrial plants. This problem can be alleviated by blending the improved partially crystalline catalyst with a non-crystalline chromia so that the catalyst may comprise essentially amorphous chromia as well as crystalline chromia. Such blended catalysts have improved toughness and can be pelleted and handled without too much difficulty. The amount of the non-crystalline (essentially amorphous) chromia additive may vary within wide limits but will usually be from about 10% to 60% by weight of the blended catalyst. The non-crystalline (essentially amorphous) chromia may itself contain a divalent metal, for example an activity promoting amount of a divalent metal such as zinc, cobalt or nickel.

The partially crystalline catalyst can be produced by sintering the corresponding amorphous or essentially non-crystalline catalyst or chromium hydroxide precursor thereof at elevated temperature under conditions whereby the apparent degree of crystallinity induced in the chromia is controlled, for example to between 8% and 50% by weight and such a process is provided according to another feature of the invention. Such a process in which the crystallised chromia is subsequently impregnated with zinc or a compound of zinc is also provides a further aspect of the invention.

Sintering may be carried out under an inert atmosphere such as nitrogen gas or in an oxidising atmosphere such as air which may optionally be diluted with an inert gas such as nitrogen. The temperature of sintering may be within the range from about 400° to 800° C., preferably from 500° C. to 600° C. in an inert atmosphere and from about 300° C. to 800° C., preferably from 330° C. to 500° C. in air. Catalysts produced by sintering in nitrogen contain the chromium as essentially only chromium (III) whilst those produced by sintering in air tend to contain some chromium (VI) as well as chromium (III). As described hereinbefore, we prefer to sinter the catalyst or precursor thereof in a mixed atmosphere of air and an inert gas such as nitrogen.

The crystallisation of chromia is an exothermic reaction and may be accompanied by a rapid rise in temperature leading to hot spots or run-away reaction unless the reaction is controlled. For this reason it is desirable to raise the temperature of the chromia to the desired sintering temperature and induce crystallisation of the chromia over a period of several hours, for example from 1 to 50 hours and preferably 4 to 12 hours. We have found that operating in this way enables us to control the reaction and the degree of crystallisation induced in the chromia.

During sintering and crystallisation, the surface area of the chromia/catalyst is reduced generally from above 100 $m^2/gm$ to below 100 $m^2/gm$, for example from 150 $m^2/gm$ to below 70 $m^2/gm$. We have found that within the range of crystallinity 8% to 50%, the surface area of the catalyst decreases with increasing crystallinity from about 70 $m^2/gm$ to about 20 $m^2/gm$. The surface area of the catalyst at any particular stage of the sintering procedure gives a guide as to the degree of crystallinity in the chromia and provides an indication of sufficient sintering. The degree of crystallinity in the catalyst can be controlled by controlling the sintering conditions.

The preferred catalysts containing a divalent metal promotor such as zinc, cobalt or nickel or compounds thereof can be produced by inducing crystallisation in a chromia catalyst already containing the divalent metal promotor or by creating the partially crystalline chromia base catalyst and subsequently impregnating it with the divalent metal promotor. Any of the known techniques for producing chromia-based catalysts can be used to produce the precursor catalyst in which crystallinity is induced.

If present, the amount of the divalent metal promotor is known in the art but as discussed hereinbefore in the case of zinc or a zinc compound the amount generally should be less than is used in amorphous chromia catalysts. Further, the optimum amount of zinc promotor to afford an increased initial catalyst activity depends upon the catalyst preparation method and generally is lower for catalysts made by impregnation of a pre-crystallised chromia base than for catalysts made by a route involving coprecipitation of chromium and zinc salts, for example hydroxides. As a guide, the optimum amount of zinc in a catalyst made by impregnation of a crystalline chrormia may be about 0.5% by weight whilst for a catalyst made by the coprecipitation route the optimum amount of zinc may be about 1% by weight.

The partially crystalline chromia catalysts of the invention may be blended with conventional amorphous chromia catalysts in order to impart physical robustness or toughness to the catalyst and enable it to be pelleted and handled without serious damage. As described hereinbefore, the amount of the conventional catalyst additive may be from about 10% to about 60% or even more of the blended catalyst.

The improved catalyst of the invention may be used in any of the fluorinaton reactions in which chromia-based catalysts are normally employed. These will usually be reactions of halogenated and particularly chlorine-containing hydrocarbons with hydrogen fluoride in the gas phase at elevated temperature. Numerous such reactions are operated commercially and amongst them may be mentioned the fluorination of halogenated aliphatic hydrocarbons containing from 1 to 6 carbon atoms, for example methylene chloride (to produce difluoro- methane, HFC 32); trichloroethylene (to produce 1,1,1,2-trifluoro -2,2-dichloroethane, HCFC 133a and 1,1,1,2-tetrafluoroethane, HFC 134a); HCFC 133a (to produce HFC 134a); perchloroethylene (to produce pentafluoroethane, HFC 125; chlorotetrafluoroethane, HCFC 124; and dichlorotrifluoroethane, HCFC 123); 1,1,2,2-tetrachloroethane (to produce HFC 134) and dichlorotrifluoroethane (to produce HFC 125). The catalyst is also useful in the removal of the impurity chlorodifluoro- ethylene (HCFC 1122) from HFC 134a by reacting the impurity with hydrogen fluoride to produce HCFC 133a. Processes employing the above starting materials are used commercially and thus are important but it is to be understood that the fluorination process according to the present invention is not limited to use of these starting materials.

Included within the invention is a process for fluorinating halogenated hydrocarbons which comprises reacting the halogenated hydrocarbon with hydrogen fluoride in the vapour phase at elevated temperature in the presence of the improved fluorination catalyst described herein. The conditions such as temperature, pressure, ratios of reactants and number of reaction steps for carrying out fluorination reactions using chromia-based catalysts are well known in the art and are generally applicable to the improved catalyst of the invention, although the increased activity of the improved catalyst generally enables lower temperatures or shorter contact times to be employed than have typically been used hitherto.

When employed in the production of hydrofluorocarbons [HFCs], the improved catalysts can suffer deactivation due to coke/carbon deposition and may require periodic regeneration. The catalysts can be regenerated as necessary by conventional regeneration techniques such as heating in air or in a mixed atmosphere of air and hydrogen fluoride and/or an inert gas. The improved catalysts afford the advantage that they require replacement less frequently than conventional chromia-based catalysts and have a longer active working lifetime.

The invention is illustrated but in no way limited by the following examples.

EXAMPLE 1

An amorphous chromia catalyst containing 1% by weight of zinc was prepared by the mixed metal hydroxide precipitation technique. 4 litres of 1 molar chromium nitrate [$Cr(NO_3)_3$] solution were added to 12 ml of 4 molar zinc nitrate [$Zn(NO_3)_2$] solution to form a mixed metal nitrate solution.

740 ml of 0.88 molar ammonia solution was prepared and stirred using an impeller and sufficient of the mixed metal nitrate solution was added to it to lower the pH to 7.3 at a temperature of 21° C. The resulting mixed metal hydroxide precipitate was collected using a flat bed filter and washed with demineralised water. The washed precipitate was dried in a nitrogen atmosphere for 12 hours at 150° C. and then calcined under nitrogen gas at 280° C. for a further 8 hours. The resulting solid was powdered, mixed with 2% by weight of graphite and formed into pellets of density 2 gm/cm$^3$. The catalyst at this stage was found to be essentially amorphous (non-crystalline) and had a surface area of 239 m$^2$/gm determined by the BET nitrogen absorption method.

The catalyst pellets were crushed and seived to generate granules of particle size 0.5–1.5 mm and 4 g of the granules was charged to a 9 mm internal diameter reaction tube for sintering. The catalyst was heated at 425° C. for 16 hours in a flow of 18 m/min of nitrogen mixed with 1 ml/min of air after which time the air flow was stopped and the catalyst was cooled to room temperature in the nitrogen flow. The catalyst was then discharged from the reactor and was found to have an apparent crystallinity of about 45% with a surface area of 57 m$^2$/gm measured by the BET nitrogen absorption method.

2 gm of the partially crystalline catalyst was re-charged to the reactor for conditioning and activity testing. The catalyst was dried at 300° C. for 30 minutes in a nitrogen flow of 50 ml/min and then was heated at 300° C. in a hydrogen fluoride flow of 20 ml/min until hydrogen fluoride was detected in the reactor vent stream. The reactor temperature was increased to 380° C. for 16 hours whilst continuing the flow of hydrogen fluoride, prior to measurement of the activity of the catalyst.

The catalyst was cooled to 350° C., still in the flow of hydrogen fluoride, and then 5 ml/min of chloro-2,2,2-trifluoroethane [HCFC 133a] was added to the hydrogen fluoride flow to generate a feed having an HF: HCFC 133a molar ratio of 4:1. After 2 hours, the catalyst temperature was reduced to 300° C. and the yield of 1,1,1,2-tetrafluoroethane [HFC 134a] at 300° C. was quantified by gas chromatographic analysis. The yield of HFC 134a at 300° C. was 17.2%

COMPARATIVE EXAMPLE A

For purposes of comparison, the activity of the unsintered catalyst was determined. 2 gm of the amorphous catalyst granules was charged into the reactor and the catalyst was dried, conditioned and tested by the procedure described above except that the sintering step at 425° C. was omitted so that the catalyst remained essentially non-crystalline. The yield of HFC 134a at 300° C. was 7.6%.

COMPARATIVE EXAMPLE B

For purposes of comparison also, an amorphous chromia catalyst containing 3% by weight of zinc was prepared as described in Example 1 using 36 ml of the zinc nitrate solution instead of 12 ml. The resulting catalyst had a surface area of 183 m$^2$/gm. The catalyst was granulated and sieved as in Example 1 and 4 gm of catalyst granules was charged to the reactor for sintering. The catalyst was heated at 400° C. for 16 hours in a flow of 5 ml/mn of air after which time the catalyst was cooled to room temperature in a nitrogen flow of 18 ml/min. The catalyst was discharged from the reactor and was found to have an apparent crystallinity of about 90% with a surface area of 23 m$^2$/gm. The amorphous and crystalline catalysts were tested as described above. Using the amorphous catalyst, the yield of HFC 134a at 300° C. was 8.6% and using the crystalline catalyst, the yield of HFC 134a at 300° C. was only 1.8%.

EXAMPLE 2

An amorphous chromia catalyst was prepared by the precipitation technique. Aqueous ammonia solution was added to an aqueous solution containing chromium to produce a precipitate of chromium hydroxide. The precipitate was washed with demineralised water, dried in a nitrogen atmosphere at 150° C. and then calcined under nitrogen at 280° C. for 8 hours. The resulting solid was powdered, mixed with 2% by weight of graphite and formed into pellets. The chromia was found to be essentially amorphous (non-crystalline) and had a surface area of 176 m$^2$/gm determined by the BET nitrogen adsorption method.

The amorphous catalyst pellets were crushed and seived to generate granules of particle size 0.5–1.4 mm and 50 gm of the granules was charged to a reaction tube for sintering. The catalyst was heated at 190° C. in a flow of 20 ml/min nitrogen gas for 2 hours and then the temperature was raised to 550° C. at the rate of 20° C./hour and maintained at 550° C. for 24 hours. The catalyst was then cooled to room temperature in the nitrogen flow and discharged from the reactor. This base catalyst was found to have an apparent degree of crystallinity of about 80% with a surface area of 47 m$^2$/gm. 4.95 gm of the base catalyst was added to 0.96 ml of aqueous zinc chloride solution (prepared by dissolving 13.54 gm of zinc chloride in demineralised water to provide 250 ml of solution) and the mixture was stirred and evaporated to dryness to give an impregnated chromia catalyst containing 0.5% by weight of zinc.

2 gm of the impregnated catalyst was charged to an Inconel reaction tube for conditioning and activity testing. The catalyst was dried at 250° C. for 90 minutes in a 50 ml/min flow of nitrogen gas and was then heated at 300° C. in a 20 ml/min flow of hydrogen fluoride until hydrogen fluoride was detected in the reactor vent stream whereupon the temperature was raised to 380° C. for 16 hours whilst the flow of hydrogen fluoride was maintained.

After conditioning as above, the catalyst was cooled to 350° C., still in the hydrogen fluoride flow and then 5.8 ml/min of 1-chloro-2,2,2-trifluoroethane [HCFC 133a] was added to the hydrogen fluoride flow to provide a feed having an HF:HCFC 133a molar ratio of 3.4:1. After two hours the catalyst temperature was reduced to about or below 300° C. The yield of 1,2,2,2-tetrafluoroethane [HFC 134a] at 297° C. and 288° C. was measured by gas chromatographic analysis. The yield of HFC 134a at 297° C was 17.4% and the yield at 288° C. was 14.1%.

EXAMPLE 3

Using the impregnation procedure described in Example 2, an impregnated chromia catalyst containing 1% by weight of zinc was prepared from 4.90 gm of base catalyst and 1.92 ml of zinc chloride solution. 2 gm of the catalyst was conditioned and tested as described in Example 2 with a yield of HFC 134a at 297° C. of 14% and a yield of HFC 134a at 288° C. of 11.5%.

EXAMPLE 4

Using the impregnation procedure described in Example 2, an impregnated chromia catalyst containing 3% by weight of zinc was produced from 4.69 gm of base catalyst and 5.77 ml of zinc chloride solution. 2 gm of the catalyst was conditioned and tested as described in Example 2 with a yield of HFC 134a at 303° C. of 7.4% and a yield at 292° C. of 6.1%.

COMPARATIVE EXAMPLE C

For purposes of comparison the activity of the base chromia catalyst (not impregnated with zinc) was determined using the conditioning and testing procedure described in Example 2. The yield of HFC 134a at 301° C. was 15% and at 283° C. was 6.4%.

What is claimed is:

1. A chromia-based fluorination catalyst comprising zinc or a compound of zinc in an amount of less than about 3% by weight of the catalyst, and having an apparent degree of crystallinity of from 8% to 50% by weight, as determined by X-ray diffraction analysis using the standard NIST technique and comparing the result obtained with that obtained by analysis of pure alpha chromia standard prepared by sintering chromia at 1223K in air for 24 hours, which catalyst is obtained by inducing crystallinity in chromia and subsequently introducing zinc or a compound of zinc into the crystallized chromia by impregnation with a solution of soluble zinc salt or by inducing crystallization in a chromia catalyst comprising zinc or a zinc compound, essentially in the absence of H$_2$ gas.

2. A catalyst as claimed in claim 1 in which the zinc or compound of zinc is present in an amount exceeding 0.1% by weight of the catalyst.

3. A catalyst as claimed in claim 1 in which the zinc or compound of zinc is present in an amount of 0.1 to 2% by weight of the catalyst.

4. A catalyst as claimed in claim 1 having a surface area greater than about 20 m$^2$/gm.

5. A chromium-based fluorination catalyst composition comprising a blend of a catalyst as claimed in claim 4 with a non-crystalline chromia catalyst.

6. A catalyst composition as claimed in claim 5 in which the amount of the non-crystalline catalyst component of the blend is from about 10 to about 60% by weight of the blended catalyst composition.

7. A catalyst as claimed in claim 1 in which the chromia exhibits an apparent degree of crystallinity of greater than 20% by weight.

8. A process for producing a fluorinated hydrocarbon, which comprises reacting a halogenated hydrocarbon with hydrogen fluoride in the vapour phase at elevated temperature in the presence of a catalyst as claimed in claim 1.

9. A process as claimed in claim 8 for producing 1,1,1,2 tetrafluoroethane by reacting 1,1,1-trifluoro-2-chloroethane with hydrogen fluoride.

10. A process for producing a chromia-based fluorination catalyst comprising zinc or a compound of zinc in an amount of less than about 3% by weight of the catalyst, which process includes the step of sintering an essentially non-crystalline chromia catalyst or precursor thereof at a temperature of from 400 to 800° C. until it has an apparent degree of crystallinity of from 8% to 50% by weight, as determined by X-ray diffraction analysis using the standard NIST technique and comparing the result obtained with that obtained by analysis of a pure alpha chromia standard prepared by sintering chromia at 1223K in air for 24 hours.

11. A process as claimed in claim 10 which crystallinity is induced in the chromia by sintering and in which zinc or compound of zinc is subsequently introduced into the crystallised chromia by impregnation with a soluble zinc salt.

12. A process as claimed in claim 11 in which the crystallinity is induced to the extent that the chromia exhibits an apparent degree of crystallinity of greater than 20% by weight.

13. A process as claimed in claim 11 in which the amount of zinc or zinc compound introduced is such that the zinc or a compound of zinc comprises an amount exceeding 0.1% by weight of the catalyst.

14. A process as claimed in claim 11 in which the amount of zinc or zinc compound introduced is such that the zinc or a compound of zinc comprises 0.1 to 2% by weight of the catalyst.

15. A process as claimed in claim 11 in which the degree of crystallinity in the chromia is controlled so as to result in a catalyst having a surface area greater than about 20 m$^2$/gm.

16. A chromium-based fluorination catalyst comprising from 0.1 but less than about 3% by weight of zinc or a compound of zinc wherein the chromia is at least partially crystalline and exhibits an apparent degree of crystallinity as represented by alpha chromia crystals of greater than 8% and less than 50% by weight and wherein the catalyst has a surface area greater than about 20 m²/gm.

17. A catalyst as claimed in claim 16 in which the zinc is present in an amount of up to 2% by weight.

18. A catalyst as claimed in claim 16 having a surface area in the range of from about 30 to about 70 m²/gm.

19. A catalyst as claimed in claim 5, wherein the non-crystalline chromia catalyst contains an activity-promoting amount of divalent metal selected form zinc, cobalt, nickel and magnesium.

20. A process for producing a fluorinated hydrocarbon, which comprises reacting a halogenated hydrocarbon with hydrogen fluoride in the vapour phase at elevated temperature in the presence of a catalyst as claimed in claim 5.

21. A process as claimed in claim 20 for producing 1,1,1,2 tetrafluoroethane by reacting 1,1,1-trifluoro-2-chloroethane with hydrogen fluoride.

* * * * *